US00PP18450P2

(12) United States Plant Patent
van Klaveren

(10) Patent No.: US PP18,450 P2
(45) Date of Patent: Jan. 22, 2008

(54) *HYDRANGEA* PLANT NAMED 'MALTISSE'

(50) Latin Name: *Hydrangea macrophylla*
Varietal Denomination: Maltisse

(75) Inventor: Ard van Klaveren, PE De Kwakel (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 11/509,516

(22) Filed: Aug. 24, 2006

(51) Int. Cl.
*A01H 5/00* (2006.01)

(52) U.S. Cl. ..... Plt./250

(58) Field of Classification Search ..... Plt./250
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Hydrangea* plant named 'Maltisse', characterized by its upright and mounded plant habit; strong roots and stems; flowering during first year of production; and large inflorescences with red purple-colored flowers.

2 Drawing Sheets

Botanical designation: *Hydrangea macrophylla.*
Cultivar denomination: 'Maltisse'.

BACKGROUND OF THE INVENTION

The present invention relates to a new and distinct cultivar of *Hydrangea,* botanically known as *Hydrangea macrophylla* and hereinafter referred to by the name 'Maltisse'.

The new *Hydrangea* is a product of a planned breeding program conducted by the Inventor in De Kwakel, The Netherlands. The objective of the breeding program was to create new strong *Hydrangea* cultivars that flower during the first year of production.

The new *Hydrangea* originated from a cross-pollination made by the Inventor in 2001 in De Kwakel, The Netherlands, of the *Hydrangea macrophylla* cultivar Leuchtfeuer, not patented, as the female, or seed, parent with the *Hydrangea macrophylla* cultivar Green Shadow, not patented, as the male, or pollen, parent. The new *Hydrangea* was discovered and selected by the Inventor as a single flowering plant within the progeny of the stated cross-pollination in a controlled environment in De Kwakel, The Netherlands in 2002.

Asexual reproduction of the new *Hydrangea* by vegetative cuttings in a controlled environment in De Kwakel, The Netherlands since 2002, has shown that the unique features of this new *Hydrangea* are stable and reproduced true to type in successive generations.

SUMMARY OF THE INVENTION

The cultivar First Red has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Maltisse'. These characteristics in combination distinguish 'Maltisse' as a new and distinct cultivar of *Hydrangea:*

1. Upright and mounded plant habit.
2. Strong roots and stems.

3. Flowers first year of production.
4. Large inflorescences with red purple-colored flowers.

Plants of the new *Hydrangea* differ from plants of female parent, the cultivar Leuchtfeuer, in the following characteristics:

1. Plants of the new *Hydrangea* have darker green-colored leaves than plants of the cultivar Leuchtfeuer.
2. Plants of the new *Hydrangea* have darker red-colored flowers than plants of the cultivar Leuchtfeuer.

Plants of the new *Hydrangea* differ from plants of female parent, the cultivar Green Shadow, in the following characteristics:

1. Plants of the new *Hydrangea* have stronger roots than plants of the cultivar Green Shadow.
2. Plants of the new *Hydrangea* have darker red-colored flowers than plants of the cultivar Green Shadow.
3. Plants of the new *Hydrangea* flower the first year of production whereas plants of the cultivar Green Shadow do not flower the first year of production.

Plants of the new *Hydrangea* can be compared to plants of the cultivar Adria, not patented. Plants of the new *Hydrangea* differ from plants of the cultivar Adria in the following characteristics:

1. Plants of the new *Hydrangea* are more freely branching than plants of the cultivar Adria.
2. Plants of the new *Hydrangea* are more freely flowering than plants of the cultivar Adria.
3. Plants of the new *Hydrangea* flower the first year of production whereas plants of the cultivar Adria do not flower the first year of production.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Hydrangea*.

The photograph on the first sheet comprises a side perspective view of a typical plant of 'Maltisse' grown in a container.

The photograph on the second sheet is a close-up view of typical inflorescences of plants of 'Maltisse'.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photographs and in the following description were grown in De Kwakel, The Netherlands, in 5-liter containers in a glass-covered greenhouse and under conditions which closely approximate commercial production conditions. During the production of the plants, day temperatures ranged from 10° C. to 30° C. and night temperatures ranged from 5° C. to 18° C. Plants of the new *Hydrangea* were about two years old when the photographs and description were taken during the late summer.

Botanical description: *Hydrangea macrophylla* cultivar Maltisse.

Parentage:

*Female, or seed, parent.*—*Hydrangea macrophylla* cultivar Leuchtfeuer, not patented.

*Male, or pollen, parent.*—*Hydrangea macrophylla* cultivar Green Shadow, not patented.

Propagation:

*Type cutting.*—By vegetative cuttings.

*Time to initiate roots.*—About three weeks at temperatures of 14° C.

*Root description.*—Fine, fibrous, strong; white in color.

*Rooting habit.*—Freely branching.

Plant description:

*Form/growth habit.*—Upright and mounded plant habit; inverted triangle. Strong lateral branches; moderately vigorous growth habit.

*Plant height.*—About 34.5 cm.

*Plant diameter or area of spread.*—About 56 cm.

*Branching habit.*—When pinched, freely branching with about ten lateral branches per plant.

*Lateral branches.*—Length: About 17.7 cm. Diameter: About 5 mm. Internode length: About 4.3 cm. Texture: Smooth, glabrous. Strength: Strong. Color: 143C.

Foliage description:

*Arrangement.*—Opposite, simple.

*Length.*—About 12.6 cm.

*Width.*—About 8.1 cm.

*Shape.*—Broadly oval to broadly elliptic to oblong.

*Apex.*—Apiculate.

*Base.*—Acuminate.

*Margin.*—Dentate.

*Texture, upper and lower surfaces.*—Rugose; glabrous.

*Venation pattern.*—Pinnate.

*Color.*—Developing foliage, upper surface: 141A. Developing foliage, lower surface: 143A. Fully expanded foliage, upper surface: Darker than 137A; venation, 144C. Fully expanded foliage, lower surface: 137C; venation, 145D.

*Petiole.*—Length: About 3 cm. Diameter: About 4 mm. Texture, upper and lower surfaces: Smooth, glabrous. Color, upper and lower surfaces: 144B.

Flower description:

*Flower type and habit.*—Single flat flowers arranged on terminal panicles; panicles large and globular. Flowers face upright to outward. Flowers persistent. Flowers not fragrant.

*Natural flowering season.*—Continuous flowering during the summer in Northern Europe. Plants flower during the first year of production.

*Flower longevity.*—Flowers last about one month on the plant.

*Quantity of flowers.*—Freely flowering; about 68 flowers per panicle; all flowers are fertile, no sterile flowers observed.

*Panicle height.*—About 10.7 cm.

*Panicle diameter.*—About 18.6 cm.

*Flower diameter.*—About 4.7 cm.

*Flower depth (height).*—About 1 cm.

*Flower buds.*—Length: About 3 mm. Diameter: About 3.5 mm. Shape: Flattened globular. Color: 157D; towards the apex, tinged with 62A.

*Petals.*—Arrangement: Four or five in a single whorl. Length: About 5 mm. Width: About 3.5 mm. Shape: Ovate. Apex: Acute. Base: Attenuate. Margin: Entire. Texture, upper and lower surfaces: Smooth, glabrous. Color: When opening and fully opened, upper surface: 64C; towards the base, 65D. When opening and fully opened, lower surface: 64D; towards the base, 65D.

*Sepals.*—Quantity per flower: Four or five in a single whorl. Length: About 2.3 cm. Width: About 2.9 cm. Shape: Broadly ovate. Apex: Rounded. Base: Obtuse. Margin: Entire. Texture, upper and lower surfaces: Smooth, glabrous. Color: When opening, upper surface: 59A to 60B tinged with 141A and 143A to 143B. When opening, lower surface: N57D; venation, 143D. Fully opened, upper surface: 60C; towards the apex, tinged with 147A to 147B or darker. Fully opened, lower surface: N57D; towards the apex, 144D.

*Pedicels.*—Angle: About 25° from vertical. Strength: Strong. Length: About 3.1 cm. Diameter: About 2 mm. Color: 59D; towards the base, 144B.

*Reproductive organs.*—Stamens: Quantity per flower: About eight. Filament length: About 4.5 mm. Filament color: 157A. Anther shape: Reniform. Anther length: About 1 mm. Anther color: 158D. Pollen amount: Scarce. Pollen color: 155A. Pistils: Pistil quantity per flower: About three. Pistil length: About 1.5 mm. Stigma shape: Lobed. Stigma color: 155B. Style length: About 0.5 mm. Style color: 155B. Ovary color: 154D.

*Seed/fruit.*—Seed and fruit development has not been observed.

Disease/pest resistance: Under commercial production conditions, plants of the new *Hydrangea* have not been observed to be resistant to pathogens or pests common to *Hydrangea*.

Temperature tolerance: Plants of the new *Hydrangea* have been shown to be tolerant to temperatures ranging from about 0° C. to about 35° C.

It is claimed:

1. A new and distinct *Hydrangea* plant named 'Maltisse' as illustrated and described.

* * * * *

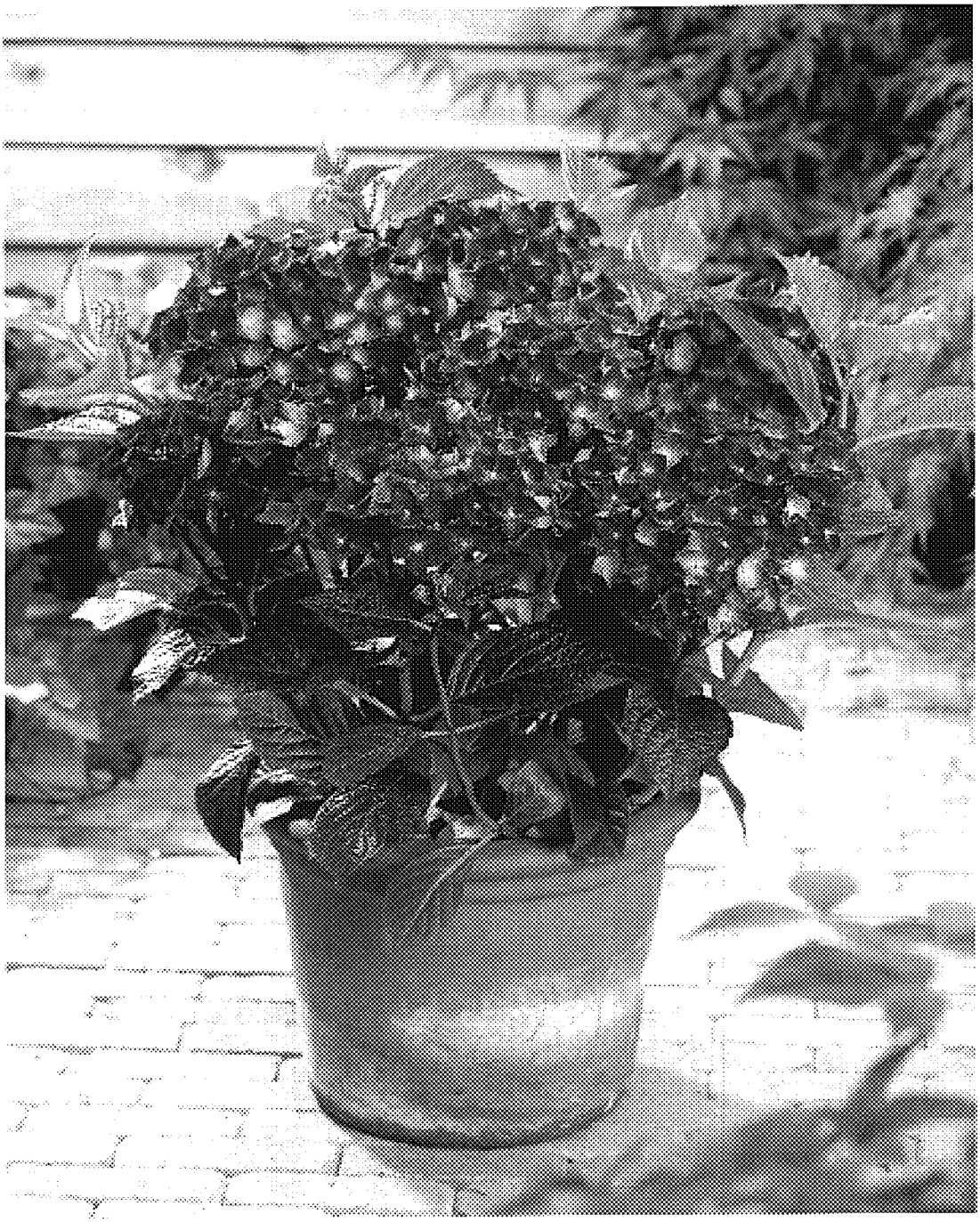

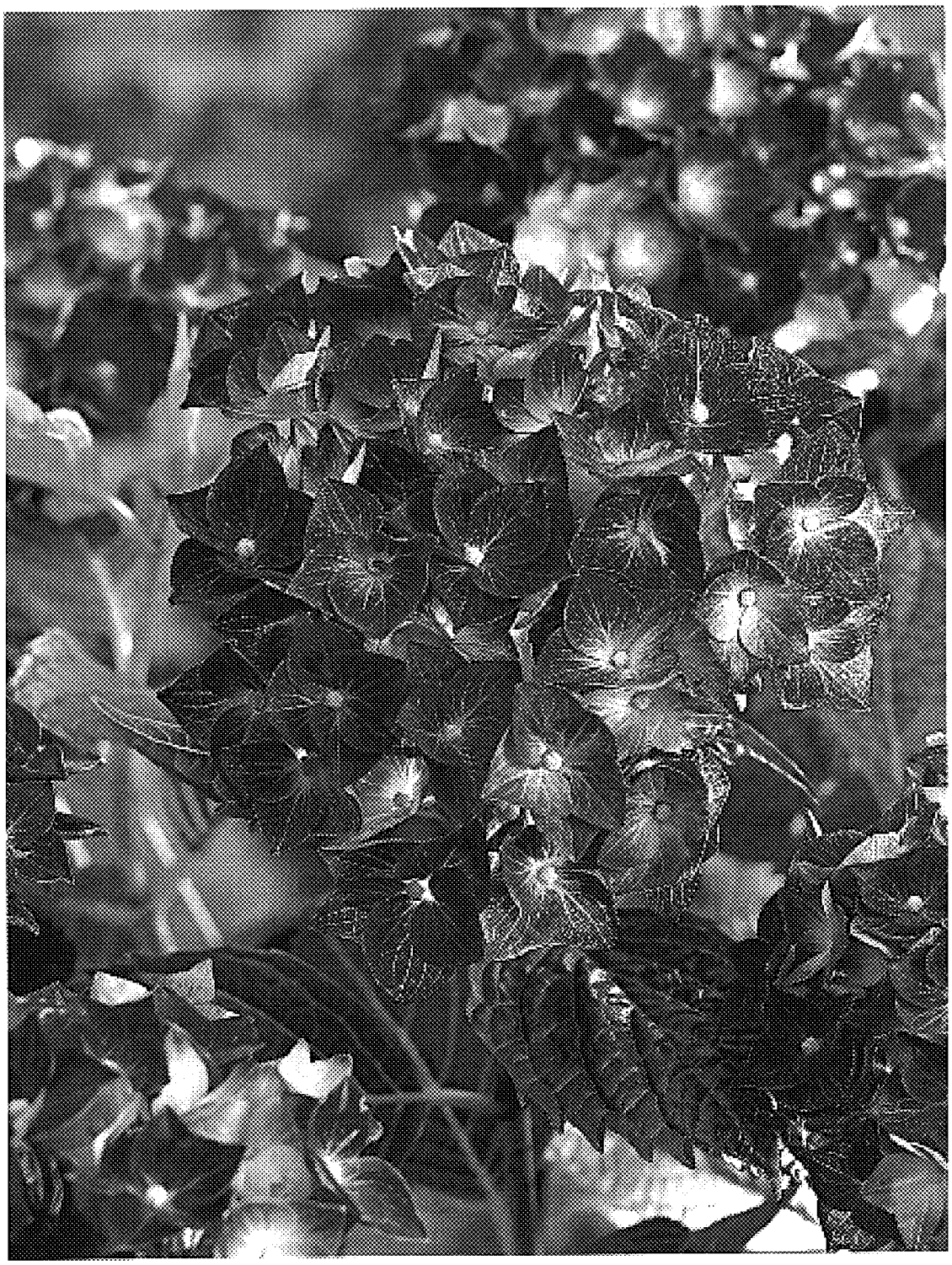

UNITED STATES PATENT AND TRADEMARK OFFICE

CERTIFICATE OF CORRECTION

PATENT NO. : PP 18,450 P2
APPLICATION NO. : 11/509516
DATED : January 22, 2008
INVENTOR(S) : Ard van Klaveren It is certified that error appears in the above-identified patent and that said Letters Patent is hereby corrected as shown below:

On the title page: Col. 1, Item (54) Title, and Item (50) should read -- HYDRANGEA PLANT NAMED "MATISSE" --.

Signed and Sealed this

Third Day of June, 2008

JON W. DUDAS
*Director of the United States Patent and Trademark Office*